US005993778A

United States Patent [19]
Firestein et al.

[11] Patent Number: 5,993,778
[45] Date of Patent: Nov. 30, 1999

[54] FUNCTIONAL EXPRESSION OF, AND ASSAY FOR, FUNCTIONAL CELLULAR RECEPTORS IN VIVO

[76] Inventors: Stuart J. Firestein, 460 Riverside Dr. #1; Haiqing Zhao, 542 W. 112th. St., both of New York, N.Y. 10027

[21] Appl. No.: 08/891,243

[22] Filed: Jul. 10, 1997

Related U.S. Application Data

[60] Provisional application No. 60/045,961, May 7, 1997.

[51] Int. Cl.⁶ .......................... A61K 48/00; A61K 49/00; G01N 33/566; G01N 33/567
[52] U.S. Cl. .......................... 424/9.1; 424/93.1; 424/93.2; 436/503
[58] Field of Search ..................... 435/6, 4, 7.2; 424/9.1, 424/93.1, 93.2; 436/503; 514/44

[56] References Cited

FOREIGN PATENT DOCUMENTS

WO 92/17585  10/1992  WIPO .

OTHER PUBLICATIONS

Crystal, RG, "Transfer of genes to humans: early lessons and obstacles to success", Science 270: 404–410, Oct. 1995.
Jolly, D, "Viral vector systems for gene therapy", Cancer Gene Therapy 1(1): 51–64, 1994.
Axel, R. The molecular logic of smell. *Scientific American* 273, 154–159 (1995).
Bakalyar, H.A. & Reed, R. R. The second messenger cascade in olfactory receptor neurons. *Curr Op Neurobiology* 1, 204–208 (1991).
Becker, T.C., et al., in Protein Expression in Animal Cells (eds. Roth, M.G.) 162–189 (Academic Press, San Diego, 1994).
Buck, L. & Axel, R. A novel multigene family may encode odorant receptors: A molecular basis for odor recognition. *Cell* 65, 175–187 (1991).
Chess, A., Simon, I., Cedar, H. & Axel, R. Allelic inactivation regulates olfactory receptor gene expression. *Cell* 78, 823–834 (1994).
Firestein, S. & Werblin F. Odor–induced membrane currents in vertebrate olfactory receptor neurons. *Science* 244, 79–82 (1989).
Firestein, S., Shepherd, G. M. & Werblin, F. S. Time course of the membrane current underlying sensory transduction in salamander olfactory receptor neurons. *J Physiol (Lond)* 430, 135–158 (1990).
Firestein, S., Picco, C. & Menini, A., The relation between stimulus and repsonse in olfactory receptor cells of the tiger salamander. *Journal of Physiology* 468, 1–10 (1993).
Gat, U., Nekrasova, E., Lancet, D. & Natochin, M. Olfactory receptor proteins—Expression, characterization and partial purification. *European Journal of Biochemistry* 225, 1157–1168 (1994).
Graham, F. L. & Prevec, L. Manipulation of Adenovirus vectors. *Meth. Mol. Biol.* 7, 109–128 (1991).
Hashimoto, M., et al. A neural cell–type–specific expression system using recombinant adenovirus vectors. *Human Gene Therapy* 7, 149–158 (1996).

Holtmaat, A. J. G. D., et al., Efficient adenoviral vector–directed expression of a foreign gene into neurons and sustentacular cells in the mouse olfactory neuroepithelium. *Molecular Brain Research* 41, 148–156 (1996).
Jones, D.T. & Reed, R. R. Golf: An olfactory neuron specific–G protein involved in odorant signal transduction. *Science* 244, 790–795 (1989).
Kanegae, Y., Makimura, M. & Saito, I. A simple and efficient method for purification of infectious recombinant adenovirus. *Jpn. J. Med. Sci. Biol.* 47, (1994).
Kanegae, Y., et al. Efficient gene activation in mammalian cells by using recombinant adenovirus expressing site–specific Cre recombinase. *Nucleic Acids Research* 23, 3816–3821 (1995).
Kim, D. G., Kang, H. M., Jang, S. K. & Shin, H. S. Construction of a bifunctional mRNA in the mouse by using the internal ribosomal entry site of the Encephalomyocarditis virus. *Molecular and Cellular Biology* 12, 3636–3643 (1992).
Lancet, D. & Ben–Arie, N. Olfactory receptors. *Current Biology* 3, 668–674 (1993).
Le Gal Le Salle, G., et al. An adenovirus vector for gene transfer into neurons and glia in the brain. *Science* 259, 988–990 (1993).
Lowe, G. & Gold, G.H. The spatial distributions of odorant sensitivity and odorant–induced currents in salamander olfactory receptor cells. *J Physiol* 442, 147–168 (1991).
Lowe, G. & Gold, G. H. Nonlinear amplification by calcium–dependent chloride channels in olfactory receptor cells. *Nature* 366, 283–286 (1993).
Miyake, S., et al. Efficient generation of recombinant adenoviruses using adenovirus DNA–terminal protein complex and a cosmid bearing the full–length virus genome. *Proc. Natl. Acad. Sci. USA* 93, 1320–1324 (1996).
Mombaerts, P., et al. Visualizing an olfactory sensory map. *Cell* 87, 675–686 (1996).
Mori, K. & Yoshihara, Y. Molecular recognition and olfactory processing in the mammalian olfctory system. *Progress in Neurobiology* 45, 585–619 (1995).
Moriyoshi, K., Richards, L. J., Akazawa, C., O'Leary, D. D. M. & Nakanishi, S. Labeling neural cells using adenovirus gene transfer of membrane–targeted GFP. *Neuron* 16, 255–260 (1996).
Ngai, J., Dowling, M. M., Buck, L., Axel, R. & Chess, A. The family of genes encoding odorant receptors in the channel catfish. *Cell* 72, 657–666 (1993).
Niwa, H., Yamamura, K. & Miyazaki, J. Efficient selection for high–expression transfectants with a novel eukaryotic vector. *Gene* 108, 193–200 (1991).

(List continued on next page.)

*Primary Examiner*—Scott D. Priebe
*Attorney, Agent, or Firm*—Fulbright & Jaworski L.L.P.

[57] ABSTRACT

Methods and materials for expressing and assaying functional neuronal receptors in neuronal cells, including methods for detecting particular odorant ligand specificity for particular odorant receptors and methods of using such. For example, methods and materials are provided for assaying for functional odor receptors in intact nasal epithelium of mammals such as rats and mice and for using such.

55 Claims, 7 Drawing Sheets

OTHER PUBLICATIONS

Ostrowski, J., Kjelsberg, M., Caron, M. & Lefkowitz, R. Mutagenesis of the beta 2–adrenergic receptor: how structure elucidates function. *Annu. Rev. Pharmacol. Toxicol.* 32, 167–183 (1992).

Ottoson, D. Analysis of the electrical activity of the olfactory epithelium. *Acta Physiol Scand* 35, 1–83 (1956).

Probst, W. C., Snyder, L. A., Schuster, D. I., Brosius, J. & Sealfon, S. C. Sequence alignment of the G–protein coupled receptor superfamily. *DNA Cell Biology* 11, 1–20 (1992).

Raming, K., et al. Cloning and expression of odorant receptors. *Nature* 361, 353–356 (1993).

Ressler, K.J., Sullivan, S.L. & Buck, L.B. A zonal organization of odorant receptor gene expression in the olfactory epithelium. *Cell* 73, 597–609 (1993).

Ressler, K.J., Sullivan, S. L. & Buck, L. B. A molecular dissection of spatial patterning in the olfactory system. *Current Opinion in Neurobiology* 4, 558–596 (1994).

Restrepo, D., Zviman, M. M. & Rawson, N.E. in Experimental Cell Biology of Taste and Olfaction (eds Spileman, A.I. & Brand, J.G.) 387–398 (CRC, Boca Raton, 1995).

Rosenfeld, M.A., et al. In vivo transfer of the human cystic fibrosis transmembrane conductance regulator gene to the airway epithelium. *Cell* 68, 143–155 (1992).

Sengupta, P., Chou, J. H. & Bargmann, C. I. odr–10 encodes a seven transmembrane receptor required for responses to the odrant diacetyl. *Cell* 84, 899–909 (1996).

Shepherd, G. M. Discrimination of molecular signals by the olfactory receptor neuron. *Neuron* 13, 771–790 (1994).

Shirley, S.G., Polak, E.H., Mather, R. A. & Dodd, G.H. The effect of concanavalin A on the rat electro–olfactogram. Differential inhibition of odorant repsonse. *Biochem J* 245, 175–184 (1987).

Sicard, G. & Holley, A. Receptor cell responses to odorants: Similarities and differences among odorants. *Brain Res* 292, 283–296 (1984).

Vanhoutte, P.M., et al. International Union of Pharmacology Committee on Receptor Nomenclature and Drug Classification. *Pharmacol. Rev.* 46, 111–116 (1994).

Vassar, R., Ngai, J. & Axel, R. Spatial segregation of odorant receptor expression in the mammalian olfactory epithelium. *Cell* 74, 309–318 (1993).

Vassar, R., et al. Topographic organization of sensory projections to the olfactory bulb. *Cell* 79, 981–991 (1994).

Watson, S.P. & Girdlstone, D. Tips on nomenclature. *Trends in Pharmacological Sciences* 16, 15–16 (1995).

Zabner, J., et al. Adenovirus–mediated gene transfer transiently corrects the chloride transport defect in nasal epithelia of patients with cystic fibrosis. *Cell* 75, 207–216 (1993).

Zhao, H., Otaki, J. M. & Firestein, S. Adenovirus–mediated gene transfer in olfactory neurons in vivo. *Journal of Neurobiology* 30, 521–530 (1996).

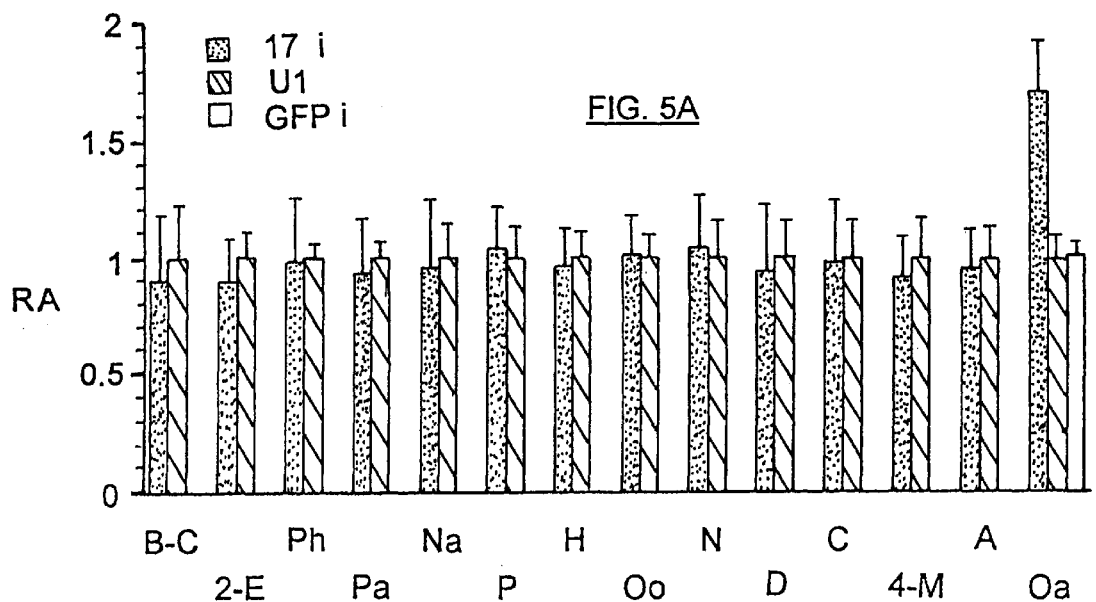
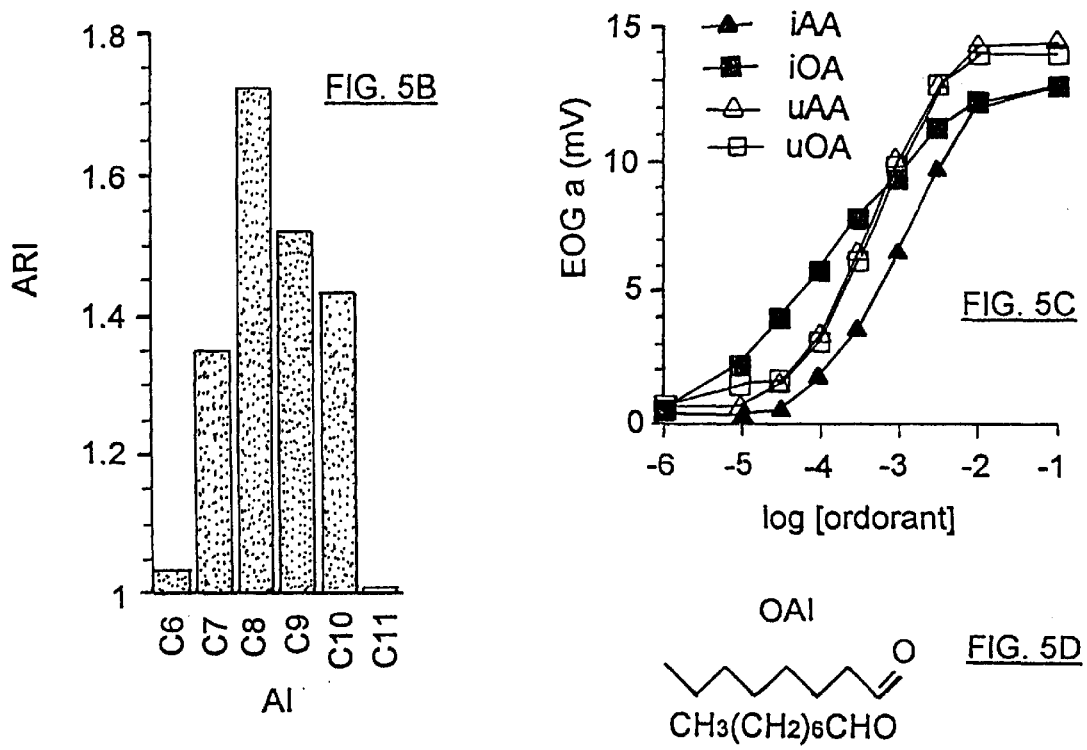

FUNCTIONAL EXPRESSION OF, AND ASSAY FOR, FUNCTIONAL CELLULAR RECEPTORS IN VIVO

CROSS-REFERENCE TO RELATED APPLICATIONS

This application claims the benefit of U.S. Provisional Patent Application No. 60/045,961 filed May 7, 1997 by Stuart J. Firestein and Haiqing Zhao, and entitled Process For Delivering, Expressing, And Assaying Neuronal Receptors In Neuronal Cells, which is hereby incorporated by reference in its entirety.

STATEMENT REGARDING FEDERALLY SPONSORED RESEARCH

This research may have been partially funded by a United States federal grant from the National Institutes of Health, National Institute on Deafness, and Other Communicative Disorders. The United States Government may, therefore, have certain rights to this invention.

BACKGROUND OF THE INVENTION

Olfactory transduction begins with the binding of an odorant ligand to a protein receptor on the olfactory neuron cell surface, thus initiating a cascade of enzymatic reactions that results in the production of a second messenger and the eventual depolarization of the cell membrane (1,2). This relatively straightforward and common signalling motif is complicated by the fact that there are several thousand odorants, mostly low molecular weight organic molecules, and nearly one thousand different receptors (3,4). The receptors are members of the superfamily of membrane receptors characterized structurally by possessing seven transmembrane spanning helices, and functionally by being coupled to GTP-binding proteins. Other members of this superfamily recognize diverse ligands from peptides to biogenic amine neurotransmitters, hormones, drugs, and other organic compounds. The odorant receptor sub-family is the largest sub-family of G-protein coupled receptors (GPCRs) but remains in some ways the most enigmatic since no particular receptor has been definitively paired with any ligand. Strictly speaking vertebrate odorant receptors are classified as "orphan" receptors—receptors with no identified ligand (5,6).

This situation is especially problematic for understanding coding in the olfactory system and appreciating the nature of the neural image passed to the brain by the peripheral transducing cells (7). Current models of olfactory processing have been driven largely by genetic data based on the now well described patterns of receptor gene expression (8,9). Receptors can be grouped into sub-families based on sequence similarities, and subfamilies of receptors are known to be expressed within one of four restricted topographic zones in the nasal epithelium, although within these general zones expression patterns appear to be random (10,11). Further, all neurons expressing a particular receptor gene converge to a restricted target in the olfactory bulb (12, 13). However, olfactory neurons typically generate physiological responses to multiple odorants (14, 15) and if, as most evidence indicates, each cell expresses only one type of receptor (11, 16), then the receptors must be able to bind a variety of molecules. Thus, while it may be attractive to hypothesize that the genetic categorization of receptor sequences reflects systematic differences in ligand specificities, and that genetic expression patterns underlie a spatial map for odorant sensitivity, experimental validation of these ideas requires knowing the correlation between receptor gene sequence and the encoded receptor protein's binding specificities, i.e. its receptive field.

Further progress in this area has been limited by the absence of a reliable and efficient system for expressing and assaying cloned odorant receptors. There appear to be two main obstacles to obtaining odorant receptor expression in a heterologous system. For one, expressed receptors must be properly targeted to, and inserted in, the plasma membrane, a process that may require specialized cellular machinery not available in heterologous cell culture expression systems. Secondly, even properly inserted receptors must couple to a second messenger system in order to produce a response that can be assayed (17). Olfactory specific isoforms of second messenger enzymes have been identified in olfactory neurons (2), raising the possibility that receptor-effector coupling may be highly specific, and that endogenous G-proteins in heterologous cell systems may be unable to produce a powerful enough response to be measured reliably.

In order to circumvent these two potential difficulties we have adopted an alternative strategy for odorant receptor expression. On the assumption that olfactory neurons themselves would be the most capable cells for expressing, targeting and coupling odorant receptors, we used the nasal epithelium as an expression system, driving expression of a particular receptor by including it in a recombinant adenovirus (Adv) and infecting rat nasal epithelia in vivo. Adenovirus vectors have been developed as a tool for efficient gene transfer in mammalian cells (18) and have shown promise in a variety of experimental and clinical applications (19–23). Here we show that this system effectively expresses a foreign odorant receptor gene that can be conveniently assayed for specific ligand activation by physiological methods. Additionally we have been able to identify a set of ligands that activate a particular receptor. This invention provides conclusive evidence that the putative odorant receptor genes cloned several years ago do indeed encode odorant receptors and, for the first time in a vertebrate, pairs a particular receptor of known amino acid sequence with a specific set of odorant ligands.

LIST OF DEFINITIONS

The following definitions are provided for illustrative purposes only and are in no way to be construed as narrowing the scope of the instant invention in any way.

Depolarize—a change in the cell membrane potential to a more positive voltage.

Action potential—a rapid transient depolarization of the cell membrane lasting 1–5 milliseconds.

Agonist—a molecule or substance that can activate a receptor protein or enzyme.

Antagonist—a molecule that binds to or otherwise interacts with a receptor to inhibit the activation of that receptor or enzyme.

Ligand—a naturally occurring or synthetic compound that binds to a protein receptor.

Odorant ligand—a ligand compound that, upon biding to a receptor, leads to the perception of an odor including a synthetic compound and/or recombinantly produced compound including agonist and antagonist molecules.

Odorant receptor—a receptor protein normally found on the surface of olfactory neurons which, when activated (normally by binding an odorant ligand) leads to the perception of an odor.

Olfactory receptor—refers to the primary sensory neuron in the nasal epithelium which responds to odors or other ligands.

Receptor—a membrane bound protein on the surface of cells that is capable of binding one or more ligands.

Functional interaction—an interaction between a receptor and ligand that results in activation of cellular responses. These may include changes in membrane potential, secretion, action potential generation, activation of enzymatic pathways and long term structural changes in cellular architecture or function.

Differentiated—refers to the final structural and functional attributes of a particular cell.

The most mature state of a cell.

Cloned—production or generation of a specific genetic sequence encoding a protein.

Recombinant—a genetic construct in which a clone has been recombined in a novel genetic environment.

Recombinantly produced receptor—a receptor protein produced by recombining its genetic sequence (clone) with other genes that induce the transcription and generation of the protein.

In vivo—refers to preparations or methods performed in a living, intact animal or organism, whether conscious or not.

In situ—refers to methods performed on tissue that remains in its normal place in the animal although the organism may be post mortem In vitro—refers to methods performed on tissues or cells that have been dissected free of an animal or are dissociated from the animal or organism. The most common example is cell culture.

SUMMARY OF THE INVENTION

The present invention relates to methods and materials for the expression and assaying of functional neuronal receptors in vivo. More particularly, the present invention relates to methods and materials for the expression and assaying of functional neuronal receptors, such as odor receptors, in neuronal cells, such as olfactory cells, in animals, such as rats. More particularly still, the present invention relates to the use of recombinant viruses, such as recombinant adenoviruses, containing odorant receptor genes, to infect olfactory cells in an assayed for specific interaction with specific odorant molecules. For example, an embodiment of the present invention uses recombinant adenovirus (Adv) encoding an odorant receptor expression cassette along with a marker gene to infect rat nasal epithelia in vito. This system effectively expresses a foreign odorant receptor gene that can be conveniently assayed for specific ligand activation by physiological methods. Additionally, this invention identifies a set of ligands that can activate a particular receptor providing a method of pairing a particular receptor of known amino acid sequence with a specific set of odorant ligands.

BRIEF DESCRIPTION OF THE DRAWINGS

FIG. 5a shows the comparison of average EOG amplitudes in AdexCAG-I7-IRES-GFP virus infected (black bar) and uninfected animals (gray bar) to 14 odorants from the panel of 74;

FIG. 5b shows I7 virus infected animals have increased odorant response to heptaldehyde (C7), octyl aldehyde (C8), nonyl aldehyde (C9), and decyl aldehyde (C10), but not to hexaldehyde (C6) nor undecylic aldehyde (C11);

FIG. 5c shows a comparison of responses (EOG amplitude) in an infected and uninfected animal to increasing concentrations of amyl acetate and octyl aldehyde;

FIG. 5d shows the chemical structure of octyl aldehyde;

DETAILED DESCRIPTION OF INVENTION

Figure 1A:
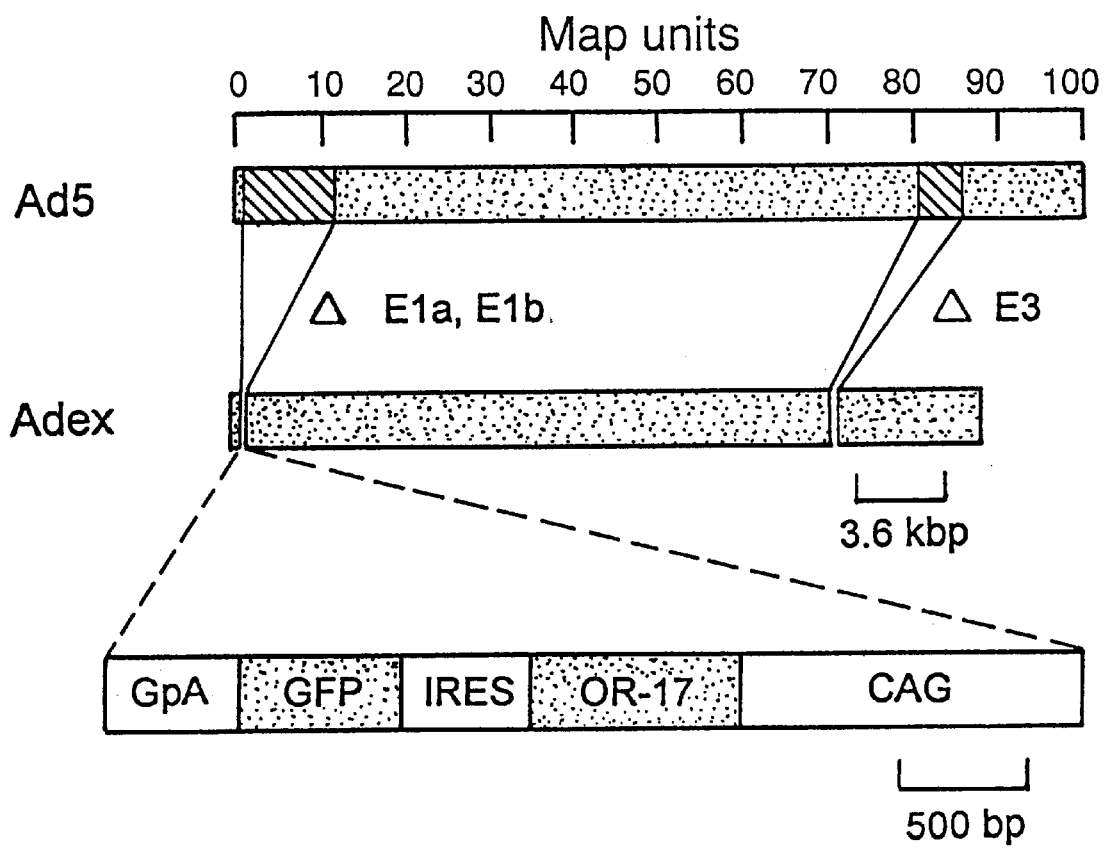
FIG. 1a illustrates the construct of the recombinant adenovirus AdexCAG-I7-IRES-GFP.

The present invention provides methods and materials for the construction of expression vectors containing cloned neuronal receptors, such as putative odor receptors, and materials and methods for the introduction of such vectors into neuronal cells (via for example, infection or transfection), such as olfactory cells, in vivo and the expression of functional cloned receptors in such cells. Further, the present invention provides materials and methods for assaying for functional receptor binding activity of such cloned receptors, including, but not limited to applications such as identifying a particular ligand for a particular receptor and/or quantitating and qualitating the binding activity of a particular receptor with a particular ligand.

The invention also provides methods and materials for identifying odorant ligands and for identifying odorant receptors. The invention further provides methods and materials for, for example, developing fragrances, identifying appetite suppressant compounds, controlling appetite, controlling insect and other animal populations, enhancing an animal's sense of smell, including to a particular odorant ligand or type of ligand including, for example, detecting specific odors such as the vapors emanating from cocaine, marijuana, heroin, hashish, angel dust, gasoline, decayed animal flesh, including human flesh, alcohol, gun powder explosives, plastic explosives, firearms, poisonous or harmful smoke, natural gas and so forth.

Methods and materials of the present invention for identifying a desired odorant ligand may comprise contacting neuronal cells, such as olfactory cells, containing a specific recombinant gene encoding and expressing a specific odorant receptor, with a series of odorant ligands to determine which ligands bind to the receptors present on the cells. Such methods may be performed in vivo and/or with cells infected in vivo and removed for in vitro assay, and/or with cells infected in vivo and removed for in vitro assay, yet the subject cells remaining situated in situ as in normal olfactory tissue.

Methods and materials of the present invention for identifying a desired odorant receptor may comprise contacting a series of neuronal cells containing a specific recombinant gene encoding and expressing a specific odorant receptor, with a known odorant ligand and determining which odorant receptor binds with the odorant ligand.

An embodiment of the present invention provides a method of detecting an odor which comprises: a) identifyng an odorant receptor which binds the desired odorant ligand and b) imbedding the receptor in a membrane such that when an odorant ligand binds to the receptor so identified, a detectable signal is produced. Examples of such detectable signals are membrane potential changes, electrophysiological methods including, but not limited to, extracellular recording-measuring changes in membrane potential from multiple cells by use of an electrode placed near to, but outside of the cells; intracellular recording-measurement of membrane potential of a single cell by inserting a fine tipped electrode into the cell interior; recording en passant, or suction electrode recording-measurement of electrical activity in a single cell by placing a blunt electrode tightly against the surface membrane of a cell, but not penetrating the cell interior; whole cell patch clamp recording-measurement of membrane potential or ion current flow in a single cell by means of an electrode which has access to the cell interior, and single channel patch recording-measurement of the ion currents passing through one or a few ion channels in an isolated patch of membrane removed from a cell with a specialized electrode. In one embodiment, of the invention, the membrane used in this method is cellular, including a membrane of an olfactory cell or a synthetic membrane.

The ligand tested for may be the vapors emanating from cocaine, marijuana, heroin, hashish, angel dust, gasoline, decayed human flesh, alcohol, gun powder explosives, plastic explosives or firearms. In another embodiment of the invention, the membrane used in this method is cellular, including a membrane of an olfactory cell or a synthetic membrane.

The ligand tested for may be the vapors emanating from cocaine, marijuana, heroin, hashish, angel dust, gasoline, decayed human flesh, alcohol, gun powder explosives, plastic explosives or firearms. In another embodiment, the ligand tested for may be natural gas, a pheromone, toxic fumes, noxious fumes or dangerous fumes.

In one embodiment of this method, the detectable signal is a measurement of the change in the transepithelial potential (or membrane potential) across the cells' surface due to the interaction of ligand and receptor. The invention may further provide a method of quantifying the amount of an odorant ligand present in a sample, and/or the affinity of the receptor for the ligand, which comprises utilizing the above-mentioned method for odor detection and then quantifying the amount of signal produced.

The invention further provides a method for developing fragrances which comprises identifying a desired odorant receptor by the above-mentioned method, then contacting cells containing and expressing the cloned odorant receptor in the above-described method with various ligands in order to determine which compounds bind the receptor and the characteristics of this binding.

The method can also provide a method for identifying an "odorant fingerprint" which comprises contacting a series of cells containing and expressing known odor receptors with a desired sample, and determining the type and quantity of the odorant ligands present in the sample.

The invention also provides a method for identifying odorant ligands which inhibit the activity of a desired odorant receptor (for example a receptor agonist or antagonist) which comprises contacting the desired odorant receptor with a series of compounds and determining which compounds inhibit the odorant ligand-odorant receptor interaction.

The methods and materials of the invention can also be used in, for example, methods for identifying appetite suppressant compounds and using same to suppress and/or control appetite; trapping odors of a specific type; controlling pest populations by, for example, identifying alarm odorant ligands and spraying same in areas in order to deter pests (such as insects, mice or rats) and/or using the inventive methods and materials to interfere with pest reproduction; as a method for promoting fertility or inhibiting fertility; and, for example, in creating animals, such as sniffing dogs, that are especially sensitive to certain odors, such as the vapors of drugs and explosives.

Strategy for Expressing Odorant Receptors

We have relied on the large number of odorant receptors, and their approximately equal expression among the six million neurons of the rat olfactory epithelium, to identify the average increase in response if one of these receptors could be overexpressed in the epithelium. From existing data it is reasonable to assume that each of the approximately 1000 receptors is expressed in roughly 0.1% of the total cells, so that if expression of one particular receptor could be induced in as few as 1–10% of the neurons the additional response due to activation of that receptor by its particular ligands would be relatively easy to detect.

The olfactory sensory epithelium lining the nasal cavity is a comparatively simple tissue consisting of only a single type of neuron, the olfactory receptor cell, as well as a glial cell type, the sustentacular cell. When activated by odorants the neurons depolarize and generate action potentials. This activity can be measured extracellularly as a transepithelial potential due to the summed activity of many cells—a measurement known as the EOG or electro-olfactogram (24). The amplitude of this voltage is determined by both the size of the response in individual cells and the number of cells responding. Electrical activity can also be measured by extracellular recording, intracellular recording, recording en passant, suction electrode recording, whole patch clamp recording, and single channel patch recording.

In order to induce olfactory neurons to express a particular receptor we generated an adenovirus vector, AdexCAG-I7-IRES-GFP, that contained the gene for a particular odorant receptor (rat I7(3)), and infected rat olfactory epithelia in vivo by direct application of a buffer containing the viral particles to the surface of the epithelium. Adenovirus, the carrier of the common cold, is a DNA virus that is known to infect epithelia of the respiratory tract (20, 21). The E1 region of the viral genome is required for viral replication (see, FIG. 1); its removal renders the virus replication incompetent and provides space for the insertion of foreign DNA. This recombinant virus can be produced in the complementary HEK 293 cell line which contains the E1 adenovirus genes (see Example 1). However, the viral particles produced are capable only of a single infection and cannot replicate in other host cells. From earlier work using an adenovirus containing the lacZ marker gene (encoding βgaluctosidase, a histochemical marker), a strong, but heterogeneous, viral infection and protein expression in rat nasal epithelium has been observed(25, 26). To facilitate electrode placement and maximize the electrical signal, or to easily locate individual transfected cells, it is useful to know the particular regions on the epithelium in which the virally delivered receptor is expressed in any individual animal. Therefore, a visible or other cellular marker can be expressed, for example, the gene for the physiological marker green fluorescent protein (GFP) was inserted in the expression cassette of Example 1 (see, FIG. 1). Because of concerns that a receptor-GFP fusion protein might alter protein expression or function, we utilized an IRES (internal ribosomal entry site) insert to produce a bicistronic message (27, this reference is hereby incorporated by reference in its entirety) that would result in the expression of odorant receptor and GFP as separate proteins in the same cells. We selected the rat I7 odorant receptor (3) for expression, but any receptor should work in this system.

The following Examples are intended to illustrate the embodiments of the present invention and are not in any way intended to limit the scope of the invention in any manner.

EXAMPLE 1
Adenoviral Vector Construction

FIG. 1a illustrates the construct of the recombinant adenovirus AdexCAG-I7-IRES-GFP. The replication-defective adenovirus expression vector Adex consists of the human adenovirus type 5 (Ad5) genome lacking the E1a, E1b and E3 regions. AdexCAG-I7-IRES-GFP has a bicistronic expression unit including the CAG promoter (CAG), composed of the cytomegalovirus enhancer plus the chicken beta-actin promoter, odorant receptor I7 (OR-I7) coding sequence, internal ribosomal entry site (IRES), the fragment for the S65T mutant of green fluorescent protein (GFP), and rabbit beta-globin polyadenylation signal (GpA). The CAG promoter drives transcription of the bicistronic message I7-IRES-GFP producing I7 odorant receptor and GFP as separate proteins. Any other suitable transfection vector can be used, as will be appreciated by one skilled in the art.

The entire odorant receptor coding sequence was amplified by polymerase chain reaction (PCR) (see, FIG. 1b), using the pfu DNA polymerase (Stratagene) from the I7 clone plasmid provided by Dr. L. Buck with the upstream primer:

SEQ ID NO. 1 5' CCCTCGAGTATGGAGCGAAGGAAC-CAC 3'
and the downstream primer:
SEQ ID NO. 2 5' GCTCTAGACTAACCAATTTTGCT-GCCT 3'

The 0.6 kb internal ribosomal entry site (IRES) fragment (27) was cut with EcoRI and BamHI from plasmid p1162 provided by Dr. Thomas Lufkin. The fragments of I7, IRES and the S65T mutant of green fluorescent protein (GFP) were first conjugated in the polycloning sites of the expression vector pCA4 (Microbix, Ontario, Canada) and tested by Northern blot with an I7 probe for transcription of mRNA, and green fluorescence for IRES-driven GFP expression in human embryonic kidney (HEK) 293 cells (ATCC, CRL-1573).

The I7-IRES-GFP sequence was then subcloned into the SwaI site of the cosmid vector pAdex1pCAw (38, 39). The pAdex1pCAw cosmid was created from the human adenovirus type 5 genome from which the E1a, E1b, and E3 regions were deleted and replaced with an expression unit containing the CAG promoter (composed of the cytomegalovirus enhancer plus the chicken beta-actin promoter (40)), a SwaI site, and the rabbit beta-globin polyadenylation signal. The I7 sequence in the cosmid vector pAdexI7-IRES-GFP was confirmed by sequencing. The cosmid vector pAdexI7-IRES-GFP and the EcoT22I digested DNA-terminal protein complex (DNA-TPC) (41) of Ad5-dlx which is a human type 5 adenovirus lacking the E3 region were co-transfected into HEK 293 cells by calcium phosphate precipitation. The recombinant adenovirus AdexCAG-I7-IRES-GFP was then generated by homologous recombination in the HEK 293 cells. The DNA-TPC method has been described in detail in refs. 39 and 41 (these references are hereby incorporated by reference in their entirety). BamHI and XbaI digestion of the genomic DNA of AdexI7-IRES-GFP produced the appropriate band pattern, and positive PCR amplification of I7 also verified the construct (see, FIG. 1b). Since recombinant viruses do not include the E1a genes, PCR amplification of the E1a region was performed with the primers:

SEQ ID NO 3: 5' ATTACCGAAGAAATGGCCGC 3'
and
SEQ ID NO 4: 5' CCCATTTAACACACGCCATGCA 3'
as a control for contamination by wild type adenovirus (Ad5-dlX).

Figure 1B:
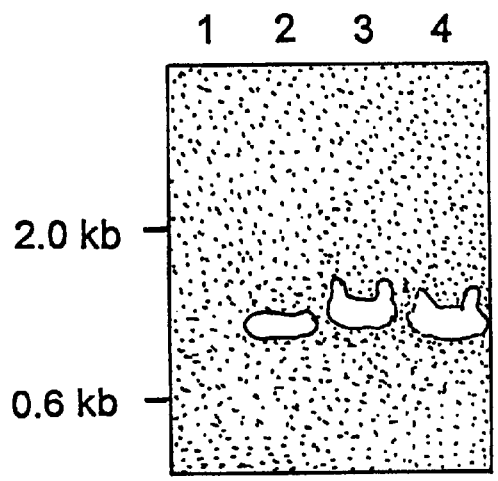
FIG. 1b shows the PCR amplification of E1a and I7 from AdexCAG-I7-IRES-GFP viral DNA.

FIG. 1b shows the PCR amplification of E1a (lane 1) and I7 (lane 2) from AdexCAG-I7-IRES-GFP viral DNA. The completely negative amplification for E1a confirmed the absence of the wild type adenovirus contamination. The positive amplification for I7 (Lane 2) and restriction enzyme digestions were used to verify the viral construct. Lanes 3 and 4 are E1a and I7 amplified from plasmids containing E1a sequence and I7 sequence respectively as the positive amplification controls. Negative PCR amplification of the E1a gene was observed in every stock of recombinant adenovirus. The recombinant adenovirus was propagated in HEK 293 cells and purified by cesium gradient centrifugation (42). The viral titer was determined by plaque forming assay on HEK 293 cells.

Techniques for performing such as the above-mentioned and some other illustrative examples herein presented, are well known to, and understood by, those skilled in the art (see, for example, PCT Application No. PCT/US92/02741 (WO 92/17585) which is hereby incorporated by reference in its entirety).

EXAMPLE 2
Infection and Expression in Nasal Epithelia

Rats (Sprague-Dawley) of various ages and both sexes were used for these experiments. Under anesthesia (ketamine, 90 mg/kg and xylazine, 10 mg/kg, i.p.), 30 $\mu$l of rat Ringer solution (in mM, 135, NaCl; 5, KCl; 1, CaCl$_2$; 4, MgCl$_2$; 10, HEPES; pH 7.4) containing the AdexCAG-I7-IRES-GFP at a titer of $3\times10^9$ pfu/ml, and 0.3% fast green dye was slowly injected through the nostril into the right side of the nasal cavity with a short length of thin plastic tubing. The solution was allowed to remain in the nasal cavity. After recovery, the animals were maintained at room temperature with no other treatment until sacrificed.

Figure 2A:
FIG. 2a shows the side view of the medial surface of the rat nasal, turbinates.

Approximately 30 $\mu$l of buffer containing the purified recombinant adenovirus, AdexCAG-I7-IRES-GFP, at a titer of $3\times10^9$ pfu/ml was irrigated into the nasal cavity of anesthetized rats of varying ages and sex. The animals were sacrificed 3–8 days later and the nasal cavity opened, exposing the medial surface of nasal turbinates (see, FIG. 2a). FIG. 2a shows the side view of the medial surface of the rat nasal turbinates. The turbinates are labeled with Roman numerals. Dorsal is up, anterior to the left. This animal was infected by AdexCAG-I7-IRES-GFP (scale bar=3 mm).

The olfactory turbinates were dissected out and fixed with 4% paraformaldehyde in phosphate buffered saline (PBS, pH 7.4) for 2 hours and cryoprotected in 20% sucrose. 15 μm cryostat sections were cut and incubated with the polyclonal antibody for GFP (CLONTECH Laboratories). Specific staining was then visualized by using Vectastain Elite ABC kit (Vector Lab.)

Figure 2B:
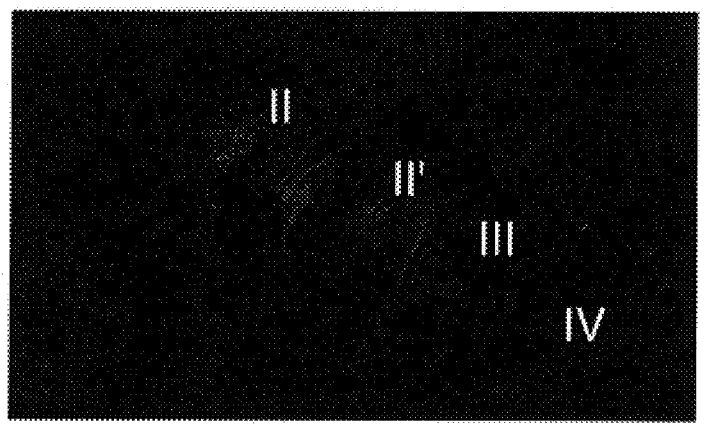
FIG. 2b shows the fluorescent micrograph of the same tissue as in FIG. 2a showing the heterogeneous expression of GFP which marked the location and the degree of virus infection.
Figure 2C:
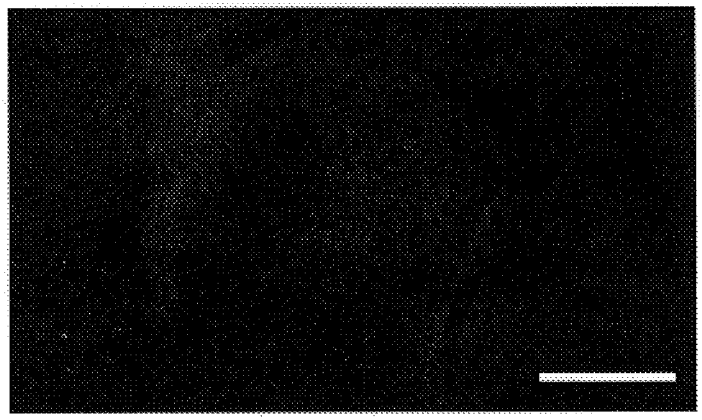
FIG. 2c shows higher magnification view of the I7 virus infected endoturbinate II' in FIG. 2b.

Under fluorescent illumination the GFP could be visualized easily (see, FIGS. 2b and 2c), clearly marking the pattern of viral infection and protein expression. FIG. 2b shows the fluorescent micrograph of the same tissue as in FIG. 2a showing the heterogeneous expression of GFP which marked the location and the degree of virus infection (scale bar=3 mm). FIG. 2c shows higher magnification view of the I7 virus infected endoturbinate II' in FIG. 2b. In regions of high fluorescence we estimate that infection rates were near 10% of neurons (scale bar=1 mm).

In some regions of the epithelia as many as 20% of the neurons were infected, while in others there was virtually no sign of infection. Overall about 1–2% of the sensory neurons were infected and expressed the GFP gene product. The highest infection rates were typically found in the second and third turbinates, usually near the edges (see, FIG. 2c).

EXAMPLE 3
Detection of Bicistronic mRNA Expression of the I7 Receptor and GFP

Expression of the bicistronic mRNA for the I7 receptor and GFP was verified by Northern blot of the infected epithelia. Northern blot detection of I7 mRNA was performed using a standard procedure (43). Total RNAs were extracted from tissues with TRIzol reagent (GibcoBRL). 20 μg of total RNA was loaded on each lane of the gel. The I7 probe was synthesized by PCR with primers that covered the entire I7 coding sequence, and labeled with Digoxigenin (DIG-11-dUTP, Boehringer Mannheim) according to the manufacturer's protocol. After hybridization the probe was detected with the DIG Nucleic Acid Detection Kit (Boehringer Mannheim).

Figure 2D:
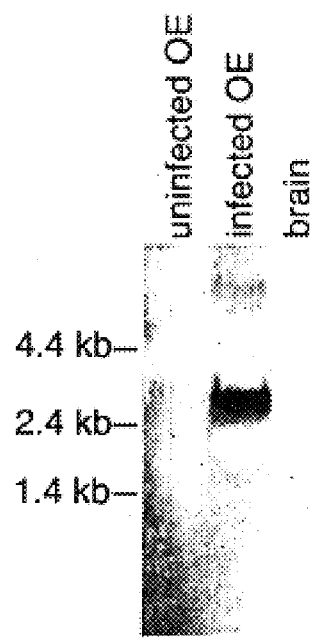
FIG. 2d shows the Northern hybridization of total RNA from uninfected olfactory epithelia, AdexCAG-I7-IRES-GFP virus infected olfactory epithelia and rat brain with I7 probe.

Using a probe that covered the entire sequence of the I7 gene we detected a single band of about 3 kb in infected, but not in uninfected epithelia where it is presumably below the level of detection (see, FIG. 2d). FIG. 2d shows the Northern hybridization of total RNA from uninfected olfactory epithelia (uninfected OE), AdexCAG-I7-IRES-GFP virus infected olfactory epithelia (infected OE) and rat brain with I7 probe. 20 micrograms of total RNA from each tissue were loaded in each lane. Examination of 28S and 18S rRNA confirmed the integrity of the RNA.

Figure 2E:
FIG. 2e shows a cryosection of AdexCAG-I7-IRES-GFP infected olfactory epithelium reacted with an antibody for GFP showing stained olfactory neurons with characteristic morphology.

Although this does not provide a quantitative measure of the extent of mRNA expression, it does provide clear evidence that expression of the I7 receptor message is much higher in infected versus uninfected tissue. For our purposes the precise rate of mRNA transcription may not be critical since the number of cells making cloned receptor has a greater effect on the EOG than the amount of receptor being made by any single neuron. This is because the gain amplification of the second messenger system in olfactory neurons assures that even the activation of a few receptors by ligand will produce a significant sensory current in individual cells. This is evident in recordings from single cells where odorant induced currents in virus infected cells are comparable to those in normal cells (see below). In the absence of antibodies specific for the I7 odorant receptor, we utilized GFP antibodies to further verify that, as with the lacZ adenovirus, the infection rate was much greater in the olfactory sensory neurons than in sustentacular cells (see, FIG. 2e). FIG. 2e shows a cryosection (15 μm) of AdexCAG-I7-IRES-GFP infected olfactory epithelium reacted with an antibody for GFP showing stained olfactory neurons with characteristic morphology, including soma (arrowhead) and single dendrite (arrow), and position within the olfactory epithelium. ML, mucous layer; OE, olfactory epithelium; BL, basal lamina (scale bar=50 μm). Thus areas of high GFP fluorescence signal the positive infection of sensory neurons.

EXAMPLE 4
Electro-olfactogram (EOG) Recording

The animal was overdosed with anesthetics (Ketamine and xylazine) and decapitated. The head was cut open sagittally and the septum was removed to expose the medial surface of the olfactory turbinates (44 this reference is hereby incorporated by reference in its entirety). The right half of the head was mounted in a wax dish filled with rat Ringer. The medial surface of turbinates was face up and exposed to the air. A continuous stream of humidified clean air was gently blown on the turbinates through tubing to prevent tissue from drying. The opening of the tubing was 8 mm in diameter and placed approximately 10 mm from the turbinate surface.

Odorant solutions were prepared by diluting a 0.5 M stock in DMSO with water. All odorant chemicals were purchased from Aldrich, except Lyral and Lilial which were the kind gift of IFF and Harmon & Reimer Inc. Three milliliters of the odorant solution were placed in a 10 ml glass test tube and capped with a silicon stopper. The concentration of volatile odorant in the 7 cc airspace was allowed to equilibrate for more than 1 hour. All solutions were used within 8 hours. Two 18 gauge needles provided the input and output ports for the odorant containing vapor above the solution. For stimulation a 100 ms pulse of the odorant vapor at 9 psi was injected into the continuous stream of humidified air. The pulse was controlled by a Picospritzer solenoid controlled valve (General Valve). Amyl acetate was used as the reference odorant to control for the variability in responses between animals and during long recording sessions, and was delivered on every sixth trial of odorant stimulation. Three tubes of amyl acetate at $10^{-3}$M liquid concentration were used alternately in each experiment. The odorant stimulus pathway was cleaned by air between each stimulus presentation. The minimum interval between two adjacent stimuli was 1 minute.

The EOG recording electrode was an Ag/AgCl wire in a capillary glass pipette filled with rat Ringer solution containing 0.6% agarose. The electrode resistance was between 0.5 and 1 MΩ. The recording pipette was placed on the surface of the olfactory epithelium and connected to a differential amplifier (DP-301, Warner Instrument). Placement of the electrode was determined by visualizing GFP fluorescence with a modified stereomicroscope (Kramer Scientific). The EOG potential was observed on a chart recorder, recorded with a DAT tape recorder, and later transferred to computer. For most experiments two electrodes and two amplifiers were used to record EOGs from two different sites of epithelium simultaneously. All experiments were performed at room temperature (22–25° C.).

EXAMPLE 5
Odorant Responses in Infected Epithelia

One difficulty in determining the ligand specificity of odorant receptors is the enormous stimulus repertoire to be tested. Well over 2,000 odorous chemicals are cataloged, including substances from virtually all classes of organic molecules. We developed a panel of 74 odorants including aromatic and short chain aliphatic hydrocarbons with various functional groups, including aldehydes, alcohols, alkanes, esters, acids, ketones, esthers and amines. For a complete list of the odorants tested, see Table 1. This list is by no means to be construed as a comprehensive list of candidate ligands but is provided merely for illustrative purposes.

types observed. OB is the olfactory bulb. The dashed line running diagonally across the epithelium indicates the border between sensory and non-sensory respiratory epithelia.

TABLE I

List of Odorants Tested

AROMATICS

| Aldehydes | Alcohols | Ketones | Ethers |
|---|---|---|---|
| para-Anisaldehyde | Cinnamyl alcohol | Aceto phenone (-) | Anisole |
| Carvone | Eugenol | 2-Decalone | Cineole |
| Cinnamaldehyde | Guaiacol |  | 2-Methylanisole |
| Salicylaldehyde |  |  | 4-Methylanisole |
| Lilial |  |  | Isoeugenol |
|  |  |  | Methyleugenol |

| Esters | Hydrocarbons | Heterocycles |
|---|---|---|
| Cinnamylformate | ortho (2)-Ethyltoluene | 2-Isobutyl-3-methoxypyrazine |
| Geranyl acetate | meta (3)-Ethyltoluene |  |
| Isoamyl salicylate | ortho(1,2)-Diethylbenzene |  |
| Linalyl formate | Limonene |  |

ALIPHATICS

| Acids | Aldehydes | Alcohols |
|---|---|---|
| Octanoic acid | Propion aldehyde | n-Propyl alcohol |
| n-Pelargonic Nonanoic acid | Isobutyr-aldehyde | n-Butyl alcohol |
| Propionic acid | n-Hexyl aldehyde | n-Pentyl alcohol |
| n-Valeric acid | n-Heptaldehyde | n-Hexyl alcohol |
|  | n-Octyl aldehyde | n-Heptyl alcohol |

| Alkanes | Amines | Esters |
|---|---|---|
| n-Octane | Isopentylamine | Amyl acetate |
| n-Nonane | Phenethylamine | Ethyl butyrate |
| n-Decane |  | Ethyl hexanoate |
|  |  | Isoamyl acetate |
|  |  | Octyl butyrate |
|  |  | Octyl isovalerate |

| Ethers | Ketones | Other |
|---|---|---|
| Citral diethyl acetal | 2,3-Butanedione | Heptyl cyanide |
| Citral dimethylacetal | 1-Fenchone | 1,1,3,3-Tetramethylbutyl isocyanide |
|  | 2-Nonanone | isocyanide |

Odorants were prepared and applied in the following manner. Three milliliters of each odorant solution at a particular concentration were placed in a 10 ml test tube stoppered with a silicone cap, and left for one hour to allow the concentration of volatile odorant in the 7 cc airspace above the solution to equilibrate. Most of the odorants were prepared at a liquid concentration of $10^{-2}$ M to $10^{-3}$ M depending on their relative volatilities. Concentrations of stimulus produced at the olfactory epithelium could not be known, but the system reliably delivered the same amount of stimulus on each trial as there was little variability between responses to successive pulses of the same odorant. The absolute odorant concentration at the tissue was not critical since responses to all odorants were compared in different animals and in each animal the responses were normalized to that animal's response to amyl acetate, the standard odorant.

Figure 3:
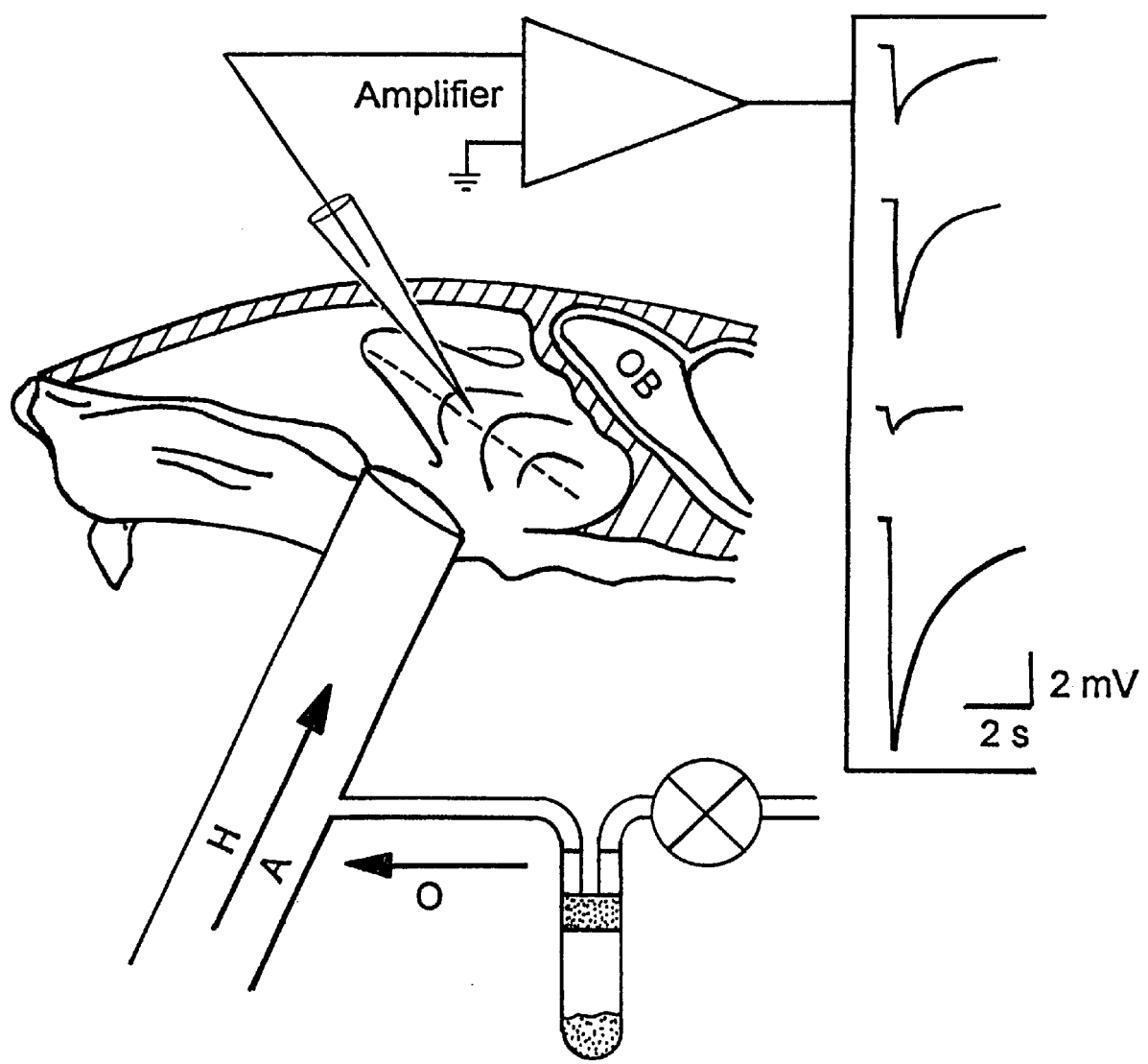
FIG. 3 shows a schematic diagram of electro-olfactogram recording and odorant stimulation system.

The stimulus delivery and EOG recording methods are pictured schematically in FIG. 3. FIG. 3 shows a schematic diagram of electro-olfactogram recording and odorant stimulation system, as described in the text. The inset shows 4 responses to odorants that represent the range of response Pulses of clean air lasting 100 msec at 9 psi were used to inject a bolus of the odorant containing vapor into a continuous stream of humidified, clean air directed at the exposed sensory epithelium. Under these conditions the tissue remained viable for up to 3 hours (although all recordings presented here were completed in under two hours), and it was possible to run twice through a panel of 30–50 odorants with each trial separated by at least 1 minute. There was no systematic difference in viability between animals of different ages or sexes, nor between infected test and non-infected control animals.

The EOG recording method, pictured schematically in FIG. 3, consists of a single glass capillary electrode connected to a differential amplifier. This electrode, placed on the epithelial surface, records transepithelial potentials that arise as a result of the depolarizing ionic currents of multiple olfactory neurons during a stimulus induced response. The EOG is recorded as a negative potential that rises rapidly to a spike-like peak which varies in maximum amplitude from less than a millivolt to as much as 15 mV, and then decays with a variable time course ranging from 1 to 5 seconds. Representative recordings of responses to several odorants from a normal rat olfactory epithelium are shown in the inset to FIG. 3. There was significant variability in the responses between animals to the various odorants, and, during long recording sessions lasting up to 2 hours, there was also variation in the responses over time. These are well known attributes of the EOG recording method, and in order to control for this variability we utilized a standard odorant, amyl acetate, to which all other odorant responses were normalized. To control for the temporal variability the amyl acetate standard was delivered every sixth trial and intervening responses were normalized to the average of the preceding and following amyl acetate responses.

Since the contribution of cells near to the electrode is greater than that from distant cells the placement of the electrode is critical. With a modified fluorescent stereomicroscope (Kramer Scientific, NY) we were able to visualize the GFP distribution and place our EOG electrode in a region of the olfactory epithelium that showed high levels of fluorescent (i.e. infected) cells. All infected animals were able to respond to all of the 74 odorants in the test panel, however responses in virally infected animals were on average 30% smaller in amplitude. Additional markers include, but are not limited to, lac-z—the gene for the bacterial enzyme beta-galactosidase, cells expressing this protein will turn a dark blue color upon reaction with the substrate X-gal; epitope tags—specialized short genetic sequences which insert a specific sequence of amino acids in a region of a protein so that the protein can be identified by antibodies directed against the "epitope tag" sequence; and fluorescent markers—including GFP and other substrates that can be caused to fluoresce when exposed to specific wavelengths of light.

Figure 4:
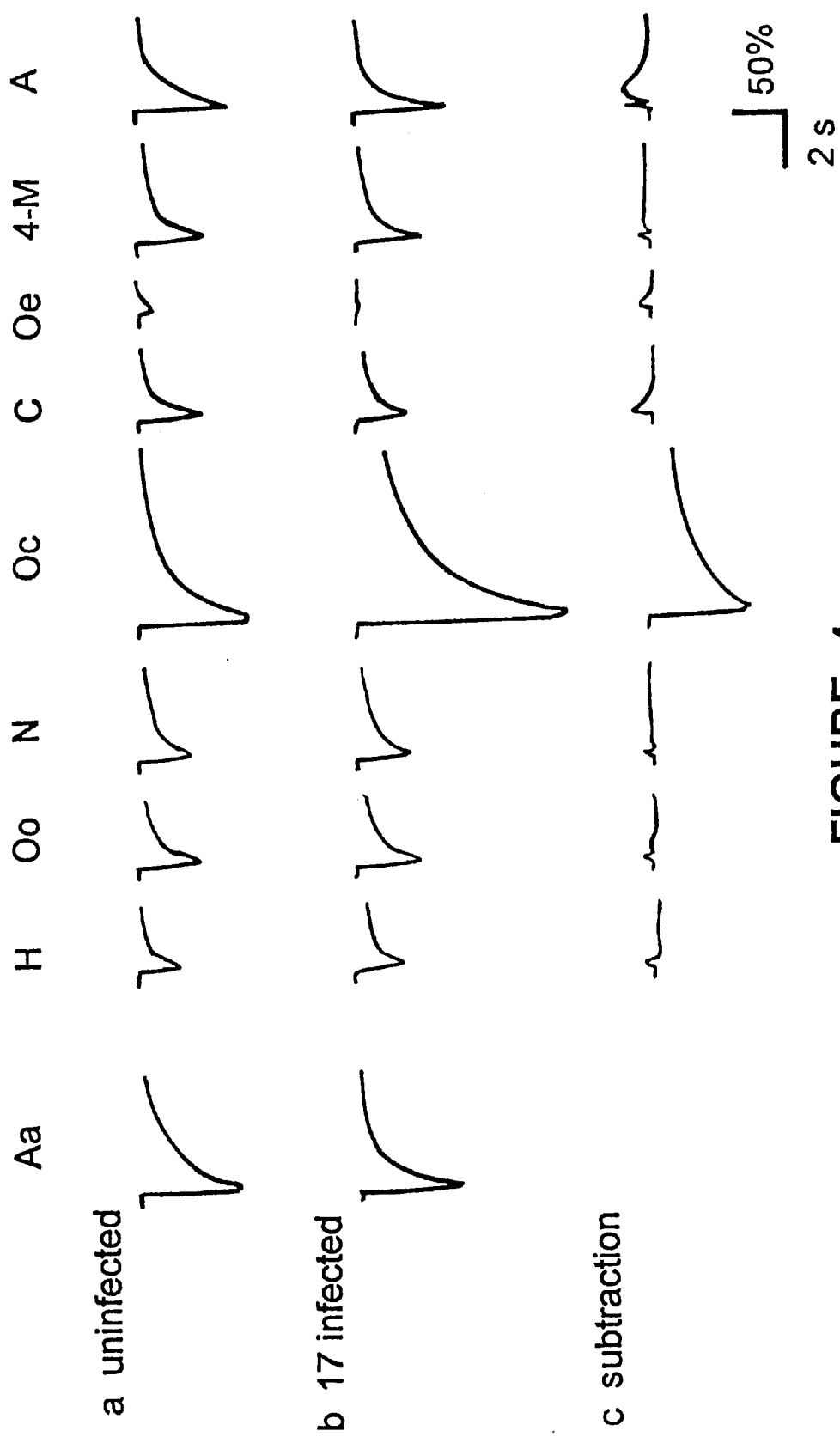
FIG. 4 shows representative EOG recordings from an uninfected (a) and an AdexCAG-I7-IRES-GFP virus infected animal (b)

Responses to 8 representative odorants from the panel of 74 odorants screened are shown in FIG. 4. FIG. 4 shows representative EOG recordings from an uninfected (a) and an AdexCAG-I7-IRES-GFP virus infected animal (b). All EOGs are responses to odorants at a solution concentration of $10^{-3}$M and are normalized to the reference odorant.

All responses are normalized to the standard (amyl acetate) odorant response which is given the value of unity. That is, all other responses are shown as the ratio of the response amplitude to the amplitude of the amyl acetate response in that animal. For 7 of the 8 odorants shown (plus the amyl acetate standard), as for 62 of the 65 other odorants in the panel, there was no significant change in responsiveness between infected and uninfected animals. However, for one odorant, octyl aldehyde or octanal, an eight carbon straight chain aliphatic aldehyde, the response is dramatically greater, both in amplitude and time course, in the infected animal. Octyl aldehyde is variously described as having a citrus, soapy and/or fatty odor quality (for the chemical structure, see FIG. 5d).

The dramatic response for octyl aldehyde in the infected animal compared to the uninfected animal can be seen even more clearly in the traces of FIG. 4c which are the result of subtracting the responses in the normal epithelium from those in the infected animal which brings out the much increased response to octyl aldehyde in the AdexCAG-I7-IRES-GFP virus infected animal. The slight positive direction of some of the subtracted traces is primarily due to differences in the time course of the responses in the different animals. The significant increase in amplitude and time course indicates that more individual olfactory neurons were responsive to octyl aldehyde in the infected versus uninfected tissue.

The average response amplitudes for 14 of the odorants from the panel of 74 are compared graphically in FIG. 5a.

FIG. 5a shows the comparison of average EOG amplitudes in AdexCAG-I7-IRES-GFP virus infected (black bar) and uninfected animals (gray bar) to 14 odorants from the panel of 74. All responses were normalized to the reference odorant, amyl acetate. The responses in uninfected animals are given the value of unity, and the responses in infected animals are scaled accordingly. As a further control, the response to octyl aldehyde was compared to that in animals infected with an adenovirus carrying only GFP (open bar). All averages are from 6 to 27 trials, error bars are the standard deviation (S.D.).

Octyl aldehyde responses are, on average, 1.7 times greater in infected vs. uninfected animals, while all other odorants are near control levels. The responses to octyl aldehyde are also compared to a control in which animals were infected with a similar amount of an adenovirus containing only the GFP gene driven by the same CAG promoter (23). Expression of GFP in these animals was comparable to that seen in animals infected with the AdexCAG-I7-IRES-GFP virus, but the response to octyl aldehyde was not different from uninfected animals. Thus, neither viral infection nor GFP alone was sufficient to generate the increase in responsivity to octyl aldehyde.

Other related odorants were tested to see if they were recognized by the I7 receptor. FIG. 5b shows I7 virus infected animals have increased odorant response to heptaldehyde (C7), octyl aldehyde (C8), nonyl aldehyde (C9), and decyl aldehyde (C10), but not to hexaldehyde (C6) nor undecylic aldehyde (C11). The bars are the result of subtraction that shows the fold increase of the average responses (n=4 to 27) to these odorants in infected animals vs. uninfected animals. Other 8 carbon aliphatic compounds with different functional groups, and at least one 8 carbon unsaturated aliphatic aldehyde, trans-2-octenal, failed to elicit responses larger than in normal animals. Thus the response profile of the I7 receptor, at least within the scope of the 74-odorant panel screened here, is relatively specific for saturated aliphatic aldehydes with straight chains between 7 and 10 carbons in length.

At the comparatively high concentrations used in these experiments the response to octyl aldehyde was on average 1.7 times greater in infected versus control animals. In fact, these high concentrations, because they are near the saturation point for the octyl aldehyde response, mask the full effect of the virally induced odorant receptor expression. FIG. 5c shows a comparison of responses (EOG amplitude) in an infected and uninfected animal to increasing concentrations of amyl acetate (AA, triangles) and octyl aldehyde (OA, squares). Heavy lines (and filled symbols) are from the infected animal, light lines (open symbols) are from the uninfected control animal. The x-axis is the log of the molar concentration of odorant solutions.

As can be seen in the close-response relations of FIG. 5c, comparison of the octyl aldehyde response to the amyl acetate at various concentrations revealed up to a 7-fold difference in response magnitude in infected versus control epithelia. For example, at an odorant concentration (in solution) of $5.\times 10^{-5}$ M, the response ratio of octyl aldehyde to amyl acetate in infected animals was 0.6:4.0 mV, 7 times larger; at the same concentration in normal animals the responses were nearly equal and the ratio was 1.

The EOG response is a function of both the number of responding cells and the response amplitude in individual cells. The relative contribution of each of these factors is not known, although as noted above, the high gain of the signal transduction cascade in the olfactory neuron makes it likely that the difference in EOG amplitudes between control and infected animals in these experiments is due primarily to an increased number of cells expressing the octanal (octyl aldehyde) sensitive receptor. In either case, the more cells near the electrode that are responding to a stimulus, the larger the response is likely to be. In particular a larger population of cells should increase both the amplitude of the response and the time course, a result that we have observed here. Moving the EOG electrode from areas of high fluorescence to regions with little or no GFP expression significantly reduced the relative amplitude of the octyl aldehyde response, but did not affect the responses to other odorants. Similarly in animals with lower infection rates, as judged by the extent of GFP induced fluorescence, responses to octyl aldehyde were comparably smaller.

EXAMPLE 6
Responses in Single Olfactory Neurons

Figure 6A:
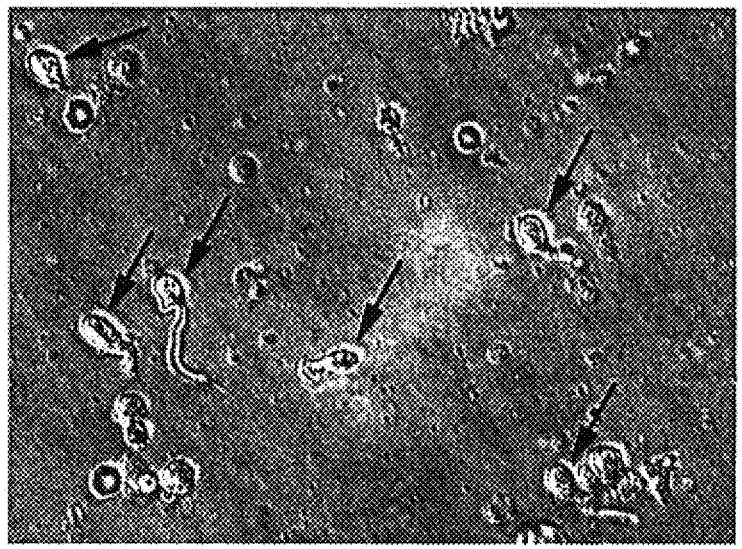
FIG. 6a shows freshly dissociated rat olfactory neurons (arrows) which can be easily identified by their morphology.
Figure 6B:
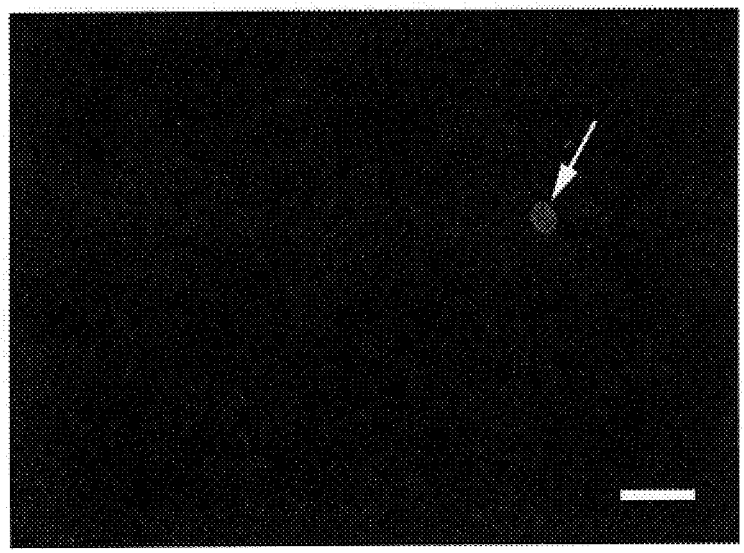
FIG. 6b shows the same field as in FIG. 6a under fluorescence illumination, an olfactory neuron infected by AdexCAG-I7-IRES-GFP virus that can be identified by expression of GFP.

Although the EOG is a simple and convenient method for efficiently screening for sensitivity to a large number of odorants, more detailed data regarding the odorant response can be obtained by recording from single olfactory neurons. Because the infected cells expressed GFP, they could be located by their fluorescence after the tissue was dissociated (see, FIGS. 6a, and 6b). FIG. 6a shows freshly dissociated rat olfactory neurons (arrows) which can be easily identified by their morphology, while FIG. 6b shows the same field as in FIG. 6a under fluorescence illumination. An olfactory neuron infected by AdexCAG-I7-IRES-GFP virus can be identified by expression of GFP (scale bar=20 $\mu$m).

Whole-cell patch clamp recording was performed on isolated cells with detectable fluorescence (FITC filter). Cell dissociation techniques for olfactory epithelium are described in detail elsewhere (45 this reference is hereby incorporated by reference in its entirety); for these experiments we included only papain treatment and mechanical disruption. Recordings were made with the Axopatch 1D amplifier. Whole-cell pipettes had a resistance of 5–10 M$\Omega$ and contained 135 mM CsCl; 1 mM CaCl2; 1 mM MgCl2; 10 mM EGTA; 10 mm HEPES; 4 mM, ATP; 0.3 mM GTP; pH 7.4. Data were acquired with the PULSE software (HEKA). Odorants were applied by a constant stream perfusion device (SF77, Warner Instruments) or by pressure pulse. The extracellular solution was the rat Ringer described above. All cells were tested to confirm that they had the normal voltage gated currents before investigating their odorant responses.

Figure 6C:
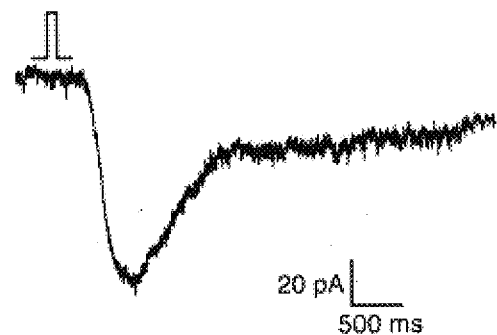
FIG. 6c shows a whole-cell patch clamp recording of a response to 0.5 mM octyl aldehyde in an infected cell.

Whole-cell patch clamp recordings from isolated GFP positive neurons revealed an octanal induced current in 5 of 5 cells (see, FIG. 6c). FIG. 6c shows a whole-cell patch clamp recording of a response to 0.5 mM octyl aldehyde in an infected cell. The holding potential was −60 mV. The currents varied from 60–250 pA in response to a 50 msec pulse of octanal at approximately 10–4 M, values that are within the range previously reported for rat olfactory neurons (28). They displayed the typical time course of odorant induced currents, including a 100–250 msec latency, a slow rise and exponential decay. The odorant induced current reversed around 0 mV. These data indicate that it is possible to record odorant induced responses due to virally transferred receptors with the resolution available in single cells.

The functional expression of a cloned odorant receptor provides a critical tool for developing an olfactory pharmacology in which odorant ligands can be correlated with specific receptors. Thus, defining the receptive field of an olfactory sensory neuron is a critical first step in understanding how olfactory perception is achieved by higher processing in the central nervous system. Additionally, because the odorant receptors, with nearly 1000 different receptor genes, make up the largest sub-family of G-protein coupled receptors (GPCRs), a pharmacology of odorant receptors could enable us to better appreciate the relation between gene sequence and binding specificity in this important class of membrane receptors.

EXAMPLE 7
Implications for Olfactory Stimulus Coding

The success of the particular strategy employed here also has several implications for the cell biology of olfactory neurons. For one, it demonstrates that olfactory neurons can express more than one odorant receptor. That they probably do not normally do this (16) appears then to result from regulation at the transcriptional level, and not from mRNA processing or translational control mechanisms. That is, there appears to be no mechanism to prevent the translation, expression and proper processing of additional odorant receptors in a sensory neuron once the mRNA is generated. On the other hand, since these receptors have not been successfully expressed in other heterologous expression systems, it does appear likely that olfactory neurons possess some cellular machinery specifically involved in the targeting and insertion of receptor proteins into the membrane. This should not be surprising from the physiological determination that odorant sensitivity is largely limited to the cilia (29, 30), suggesting that perhaps the same molecular processes are also at work concentrating transduction enzymes in the ciliary compartment. We have used receptor clones that cover only the coding sequence of the receptor molecule, indicating that untranslated signal sequences are not essential.

It also appears that the odorant receptors may require a specific G-protein for effective coupling and signal transmission. $G_{olf}$ is a $G_s$ type of G-protein, but its expression is restricted almost entirely to olfactory neurons (31). One of the characteristics of the family of odorant receptors that distinguishes them from other GPCRs is a particularly short third intracellular loop between transmembrane domains 5 and 6 (3). This loop has been implicated in receptor G-protein interactions in other GPCRs (32) and in the odorant receptors is only I7 residues long, compared to 25–40 in other members of the superfamily (33). One earlier attempt to express odorant receptors (in sf9 cells) resulted in very small responses that saturated at low levels of second messenger production, indicating a possibly weak coupling between receptor and endogenously available G-proteins (34). In the native olfactory neurons, as used in our strategy, a foreign odorant receptor appears to have no difficulty coupling to the endogenous pathway, as demonstrated by the responses in single cells that are well within the normal size range for physiological odorant responses (28).

The panel of odorants used to screen infected epithelia (see, Table 1) was drawn from an extensive physiological and psychophysical literature on odorant sensitivities. The odorants chosen were intended to represent a large range of odorant qualities and chemical types. In the only other recent study in which such an extensive series of odorants were utilized, responses to odorants applied to intact olfactory epithelium were recorded in mitral cells of the rabbit olfactory bulb (35). The mitral cell is the second order neuron onto which olfactory sensory neurons synapse in the region of neuropil known as glomeruli. Mitral cells, each with dominant input from a single type of olfactory receptor neuron, were found to have response profiles not unlike those observed here for the I7 receptor. That is, one particular odorant was usually the most effective at stimulating the mitral cell, but odorants with related structures were also excitatory, although to a lesser degree. One important difference was that for mitral cells the carbon chain length appeared to be more critical than the functional group in determining stimulus efficacy.

We found that 7, 8, 9 and 10 carbon saturated aldehydes were ligands for this receptor. Aldehydes with chains of less than 7 or more than 10 carbons were not ligands. Additionally other 8 carbon aliphatics with different functional groups were not ligands. This suggests that both the functional group and the carbon chain length are critical determinants of the odorant epitope. The only other odorant receptor for which a distinct ligand is known is the ODR-10 receptor in C. elegans which displays strong specificity for the chemical attractant diacetyl (36). This receptor appears more narrowly tuned than the rat receptor tested here which may reflect the very different demands placed on the nematode and mammalian olfactory systems as regards the size of the stimulus repertoire from which ligands must be discriminated.

The nearly 1000 separate genes encoding receptors in the olfactory system provide an opportunity to explore structure-function relations in the GPCR superfamily. Genes of the odorant receptor subfamily show a hypervariable region corresponding to the second through fifth transmembrane domains (3), the presumed ligand binding site in GPCRs (32). However, in some cases odorant receptors of the same subfamily differ from each other by only a few residues in this region (37). These genetically closely related receptors can now be tested to determine if small sequence differences result in significant changes in ligand sensitivity. With this tool it will be possible to identify key amino acid residues which could then be mutated in recombinant receptor constructs. Such a program could lead to a detailed, experimentally testable understanding of the relation between gene sequence and ligand binding specificity in membrane bound receptors.

The foregoing disclosure and description of the invention are illustrative and explanatory thereof, and various changes in the details of the illustrated apparatus and construction and method of operation may be made without departing from the spirit of the invention.

References

1. Firestein, S. & Werblin, F. Odor-induced membrane currents in vertebrate olfactory receptor neurons. *Science* 244, 79–82 (1989).
2. Bakalyar, H. A. & Reed, R. R. The second messenger cascade in olfactory receptor neurons. *Curr Op Neurobiology* 1, 204–208 (1991).
3. Buck, L. & Axel, R. A novel multigene family may encode odorant receptors: A molecular basis for odor recognition. *Cell* 65, 175–187 (1991).
4. Lancet, D. & Ben-Arie, N. Olfactory receptors. *Current Biology* 3, 668–674 (1993).
5. Vanhoutte, P. M., et al. International Union of Pharmacology Committee on Receptor Nomenclature and Drug Classification. *Pharmacol. Rev.* 46, 111–116 (1994).
6. Watson, S. P. & Girdlstone, D. TIPS on nomenclature. *Trends in Pharmacological Sciences* 16, 15–16 (1995).
7. Shepherd, G. M. Discrimination of molecular signals by the olfactory receptor neuron. *Neuron* 13, 771–790 (1994).
8. Axel, R. The molecular logic of smell. *Scientific American* 273, 154–159 (1995).
9. Ressler, K. J., Sullivan, S. L. & Buck, L. B. A molecular dissection of spatial patterning in the olfactory system. *Current Opinion in Neurobiology* 4, 558–596 (1994).
10. Vassar, R., Ngai, J. & Axel, R. Spatial segregation of odorant receptor expression in the mammalian olfactory epithelium. *Cell* 74, 309–318 (1993).
11. Ressler, K. J., Sullivan, S. L. & Buck, L. B. A zonal organization of odorant receptor gene expression in the olfactory epithelium. *Cell* 73, 597–609 (1993).
12. Vassar, R., et al. Topographic organization of sensory projections to the olfactory bulb. *Cell* 79, 981–991 (1994).
13. Mombaerts, P., et al. Visualizing an olfactory sensory map. *Cell* 87, 675–686 (1996).
14. Firestein, S., Picco, C. & Menini, A., The relation between stimulus and response in olfactory receptor cells of the tiger salamander. *Journal of Physiology* 468, 1–10 (1993).
15. Sicard, G. & Holley, A. Receptor cell responses to odorants: Similarities and differences among odorants. *Brain Res* 292, 283–296 (1984).
16. Chess, A., Simon, I., Cedar, H. & Axel, R. Allelic inactivation regulates olfactory receptor gene expression. *Cell* 78, 823–834 (1994).
17. Gat, U., Nekrasova, E., Lancet, D. & Natochin, M. Olfactory receptor proteins- Expression, characterization and partial purification. *European Journal of Biochemistry* 225, 1157–1168 (1994).
18. Graham, F. L. & Prevec, L. Manipulation of viral vectors. *Meth. Mol. Biol.* 7, 109–128 (1991).
19. Becker, T. C., et al., in Protein Expression in Animal Cells (eds. Roth, M. G.) 162–189 (Academic Press, San Diego, 1994).
20. Rosenfeld, M. A., et al. In vivo transfer of the human cystic fibrosis transmembrane conductance regulator gene to the airway epithelium. *Cell* 68, 143–155 (1992).
21. Zabner, J., et al. Adenovirus-mediated gene transfer transiently corrects the chloride transport defect in nasal epithelia of patients with cystic fibrosis. *Cell* 75, 207–216 (1993).
22. Le Gal Le Salle, G., et al. An adenovirus vector for gene transfer into neurons and glia in the brain. *Science* 259, 988–990 (1993).
23. Moriyoshi, K., Richards, L. J., Akazawa, C., O'Leary, D. D. M. & Nakanishi, S. Labeling neural cells using adenovirus gene transfer of membrane-targeted GFP. *Neuron* 16, 255–260 (1996).
24. Ottoson, D. Analysis of the electrical activity of the olfactory epithelium. *Acta Physiol Scand* 35, 1–83 (1956).
25. Zhao, H., Otaki, J. M. & Firestein, S. Adenovirus-mediated gene transfer in olfactory neurons in vivo. *Journal of Neurobiology* 30, 521–530 (1996).
26. Holtmaat, A. J. G. D., et al., Efficient adenoviral vector-directed expresison of a foreign gene into neurons and sustentacular cells in the mouse olfactory neuroepithelium. *Molecular Brain Research* 41, 148–156 (1996).
27. Kim, D. G., Kang, H. M., Jang, S. K. & Shin, H. S. Construction of a bifunctional mRNA in the mouse by using the internal ribosomal entry site of the Encephalomyocarditis virus. *Molecular and Cellular Biology* 12, 3636–3643 (1992).
28. Lowe, G. & Gold, G. H. Nonlinear amplification by calcium-dependent chloride channels in olfactory receptor cells. *Nature* 366, 283–286 (1993).
29. Firestein, S., Shepherd, G. M. & Werblin, F. S. Time course of the membrane current underlying sensory transduction in salamander olfactory receptor neurons. *J Physiol (Lond)* 430, 135–158 (1990).
30. Lowe, G. & Gold, G. H. The spatial distributions of odorant sensitivity and odorant-induced currents in salamander olfactory receptor cells. *J Physiol* 442, 147–168 (1991).
31. Jones, D. T. & Reed, R. R. Golf: An olfactory neuron specific-G protein involved in odorant signal transduction. *Science* 244, 790–795 (1989).

32. Ostrowski, J., Kjelsberg, M., Caron, M. & Lefkowitz, R. Mutagenesis of the beta 2-adrenergic receptor: how structure elucidates function. *Annu. Rev. Pharmacol. Toxicol.* 32, 167–183 (1992).
33. Probst, W. C., Snyder, L. A., Schuster, D. I., Brosius, J. & Sealfon, S. C. Sequence alignment of the G-protein coupled receptor superfamily. *DNA Cell Biology* 11, 1–20 (1992).
34. Raming, K., et al. Cloning and expression of odorant receptors. *Nature* 361, 353–356 (1993).
35. Mori, K. & Yoshihara, Y. Molecular recognition and olfactory processing in the mammalian olfctory system. *Progress in Neurobiology* 45, 585–619 (1995).
36. Sengupta, P., Chou, J. H. & Bargmann, C. I. odr-10 encodes a seven transmembrane receptor required for responses to the odrant diacetyl. *Cell* 84, 899–909 (1996).
37. Ngai, J., Dowling, M. M., Buck, L., Axel, R. & Chess, A. The family of genes encoding odorant receptors in the channel catfish. Cell 72, 657–666 (1993).
38. Kanegae, Y., et al. Efficient gene activation in mammalian cells by using recombinant adenovirus expressing site-specific Cre recombinase. *Nucleic Acids Research* 23, 3816–3821 (1995).
39. Hashimoto, M., et al. A neural cell-type-specific expression system using recombinant adenovirus vectors. *Human Gene Therapy* 7, 149–158 (1996).
40. Niwa, H., Yamamura, K. & Miyazaki, J. Efficient selection for high-expression transfectants with a novel eukaryotic vector. *Gene* 108, 193–200 (1991).
41. Miyake, S., et al. Efficient generation of recombinant adenoviruses using adenovirus DNA-terminal protein complex and a cosmid bearing the full-length virus genome. *Proc. Natl. Acad. Sci. USA* 93, 1320–1324 (1996).
42. Kanegae, Y., Makidmura, M. & Saito, I. A simple and efficient method for purification of infectious recombinant adenovirus. *Jpn. J. Med. Sci. Biol.* 47, (1994).
43. Sambrook, J., Fritsch, E. F. & Maniatis, T. Molecular cloning: A laboratory manual. (Cold Spring Harbor Laboratory Press, New York, 1989).
44. Shirley, S. G., Polak, E. H., Mather, R. A. & Dodd, G. H. The effect of concanavalin A on the rat electro-olfactogram. Differential inhibition of odorant repsonse. *Biochem J* 245, 175–184 (1987).
45. Restrepo, D., Zviman, M. M. & Rawson, N. E. in Experimental Cell Biology of Taste and Olfaction (eds Spileman, A. I. & Brand, J. G.) 387–398 (CRC, Boca Raton, 1995).

What is claimed is:

1. A method for screening for ligands of a G protein-coupled odorant receptor of a mammal comprising:
    a) infecting olfactory sensory neurons in intact nasal epithelium of a test mammal in vivo with an adenoviral expression vector comprising nucleotide sequences encoding an odorant receptor and a marker protein that can be directly detected by visual inspection, thereby producing infected olfactory neurons which express both said odorant receptor and marker protein;
    b) identifying a location on said nasal epithelium comprising said infected olfactory neurons by detecting said marker protein;
    c) exposing said infected neurons in said nasal epithelium of the test mammal in situ to either a candidate compound or a standard odorant, and exposing uninfected olfactory sensory neurons in intact control nasal epithelium of a control mammal, which is the same species as the test mammal, in situ to either a candidate compound or a standard odorant;
    d) measuring an electrochemical response by said infected neurons in situ in response to said candidate compound, or to said standard odorant and by said uninfected neurons, in situ in response to said candidate compound and to said standard odorant; and
    e) comparing the measurements of said electrochemical response by said infected neurons, and by said uninfected neurons, each in response to said condidate compound relative to said standard odorant, the measurement of said uninfected neurons in response to said candidate compound relative to said standard odorant indicating whether said candidate compound is a ligand for said odorant receptor.

2. The method of claim 1, wherein said marker protein is selected from the group consisting of fluorescent markers and histochemical markers.

3. The method of claim 1, wherein said marker protein is selected from the group consisting of green fluorescent protein and β-galactosidase.

4. The method of claim 1, wherein said infected neurons and uninfected olfactory sensory neurons are exposed to said candidate compound or standard odorant in an airborne mixture.

5. The method of claim 1, wherein said infected neuron and uninfected olfactory sensory neurons are exposed to said candidate compound or standard odorant in a liquid mixture.

6. The method of claim 1, wherein said odorant receptor is odorant receptor I7.

7. The method of claim 1, wherein said odorant receptor is odorant receptor I7 and said candidate compound is selected from the group consisting of heptyl aldehyde, octyl aldehyde, nonyl aldehyde, and decyl aldehyde.

8. The method of claim 1, wherein said adenovirus is human adenovirus type 5 and said odorant receptor is odorant receptor I7.

9. The method of claim 1, wherein said electrochemical response is measured by a measurement technique selected from the group consisting of extracellular recording, intracellular recording, recording en passant, whole-cell recording using patch clamp, and single channel recording.

10. The method of claim 9, wherein the measured cells are single cells.

11. The method of claim 1, wherein said candidate compound is an aromatic.

12. The method of claim 11, wherein said candidate compound is an aldehyde.

13. The method of claim 12, wherein said candidate compound is an aldehyde selected from the group consisting of para-Anisaldehyde, Carvone, Cinnamaldehyde, Salicylaldehyde, and Lilal.

14. The method of claim 11, wherein said candidate compound is an alcohol.

15. The method of claim 14, wherein said candidate compound is an alcohol selected from the group consisting of Cinnamyl alcohol, Eugenol, and Guaiacol.

16. The method of claim 11, wherein said candidate compound is a ketone.

17. The method of claim 16, wherein said candidate compound is a ketone selected from the group consisting of Aceto phenone (−), and 2-Decalone.

18. The method of claim 11, wherein said candidate compound is an ether.

19. The method of claim 14, wherein said candidate compound is an ether selected from the group consisting of Anisole, Cineole, 2-Methylanisole, 4-Methylanisole, Isoeugenol, and Methyleugenol.

20. The method of claim 11, wherein said candidate compound is an ester.

21. The method of claim 20, wherein said candidate compound is an ester selected from the group consisting of Cinnamylformate, Geranyl acetate, Isomayl salicylate, and Linalyl formate.

22. The method of claim 11, wherein said candidate compound is a hydrocarbon.

23. The method of claim 22, wherein said candidate compound is a hydrocarbon selected from the group consisting of ortho (2)-Ethyltoluene, meta (3)-Ethyltoluene, ortho(1,2)-Diethylbenzene, and Limonene.

24. The method of claim 11, wherein said candidate compound is a heterocyclic.

25. The method of claim 24, wherein said candidate compound is 2-Isobutyl-3-metboxypyrazine.

26. The method of claim 1, wherein said candidate compound is aliphatic.

27. The method of claim 26, wherein said candidate compound is an acid.

28. The method of claim 27, wherein said candidate compound is an acid selected from the group consisting of Octanoic acid, n-Pelagonic Nonanoic acid, Propionic acid, and n-Valeric acid.

29. The method of claim 26, wherein said candidate compound is an aldehyde.

30. The method of claim 29, wherein said candidate compound is an aldehyde selected from the group consisting of Propion aldehyde, Isobutyr-aldehyde, n-Hexyl aldehyde, n-Heptaldehyde, n-Octyl aldehyde, trans-2-Octenal, 2-octynal, n-Nonyl aldehyde, n-Decyl aldehyde, Dodecyl aldlehyde, Undecylic aldehyde, trans-2-Tridecanal, Citral, n-Valeraldehyde, and Lyral.

31. The method of claim 26, wherein said candidate compound is an alcohol.

32. The method of claim 31, wherein said candidate compound is an alcohol selected from the group consisting of n-Propyl alcohol, n-Butyl alcohol, n-Pentyl alcohol, n-Hexyl alcohol, n-Heptyl alcohol, n-Octyl alcohol, n-Nonyl alcohol, n-Decyl alcohol, 2-Ethylfenchol, Geraniol, B-Citronellol, and Linalool.

33. The method of claim 26, wherein said candidate compound is a ketone.

34. The method of claim 33, wherein said candidate compound is a ketone selected from the group consisting of 2,3-Butanedione, 1-Fenchone, and 2-Nonanone.

35. The method of claim 26, wherein said candidate compound is an ether.

36. The method of claim 35, wherein said candidate compound is an ether selected from the group consisting of Citral diethyl acetal, and Citral dimethylacetal.

37. The method of claim 26, wherein said candidate compound is an alkane.

38. The method of claim 37, wherein said candidate compound is an alkane selected from the group consisting of n-Octane, n-Nonane, and n-Decane.

39. The method of claim 26, wherein said candidate compound is an amine.

40. The method of claim 39, wherein said candidate compound is an amine selected from the group consisting of Isopentylamine, and Phenethylamine.

41. The method of claim 26, wherein said candidate compound is an ester.

42. The method of claim 41, wherein said candidate compound is an ester selected from the group consisting of Amyl acetate, Ethyl butyrate, Ethyl hexanoate, Isoamyl acetate, Octyl butyrate, and Octyl isovalerate.

43. The method of claim 26, wherein said candidate compound is selected from the group consisting of Heptyl cyanide, and 1,1,3,3-Tetramethylbutyl isocyanide, and isocyanide.

44. A method for screening for ligands of a G protein-coupled odorant receptor of a mammal comprising:
   a) infecting olfactory sensory neurons in intact nasal epithelium of a test mammal in vivo with an adenoviral expression vector comprising nucleotide sequences encoding an odorant receptor and a marker protein that can be directly detected by visual inspection, thereby producing infected olfactory neurons which express both said odorant receptor and marker protein;
   b) identifying a location on said nasal epithelium comprising said infected olfactory neurons by detecting said marker protein;
   c) isolating said nasal epithelium in vitro;
   d) exposing said infected neurons in said nasal epithelium of the test mammal to either a candidate compound or a standard odorant, and exposing uninfected olfactory sensory neurons in intact control nasal epithelium of a control mammal, which is the same species as the test mammal, in situ to either a candidate compound or a standard odorant;
   e) measuring an electrochemical response by said infected neurons in situ in response to said candidate compound, or to said standard odorant, and by said uninfected neurons in situ in response to said candidate compound and to said standard odorant; and
   f) comparing the measurements of said electrochemical response by said infected neurons, and by said uninfected neurons, each in response to said condidate compound relative to said standard odorant, the measurement of said uninfected neurons in response to said candidate compound relative to said standard odorant indicating whether said candidate compound is a ligand for said odorant receptor.

45. The method of claim 44, wherein said marker protein is selected from the group consisting of fluorescent markers and histochemical markers.

46. The method of claim 44, wherein said marker protein is selected from the group consisting of green fluorescent protein and β-galactosidase.

47. The method of claim 44, wherein said infected neurons and uninfected olfactory sensory neurons are exposed to said candidate compound or standard odorant in an airborne mixture.

48. The method of claim 44, wherein said infected neurons and uninfected olfactory sensory neurons are exposed to said candidate compound or standard odorant in a liquid mixture.

49. The method of claim 44, wherein said odorant receptor is odorant receptor I7.

50. The method of claim 44, wherein said odorant receptor is odorant receptor I7 and said candidate compound is selected from the group consisting of heptyl aldehyde, octyl aldehyde, nonyl aldehyde, and decyl aldehyde.

51. The method of claim 44, wherein said adenovirus is human adenovirus type 5 and said odorant receptor is odorant receptor I7.

52. The method of claim 44, wherein said electrochemical response is measured by a measurement technique selected from the group consisting of extracellular recording, intracellular recording, recording en passant, whole-cell recording using patch clamp, and single channel recording.

53. The method of claim 52, wherein the measured cells are single cells.

54. A method for screening for ligands of a G protein-coupled odorant receptor of a mammal comprising:
   a) providing a mammal whose olfactory sensory neurons in intact nasal epithelium have been infected with an adenoviral expression vector comprising nucleotide sequences encoding said odorant receptor and a marker protein that can be directly detected by visual inspections, thereby producing infected olfactory neurons which express both said odorant receptor and marker protein and identifying a location on said nasal epithelium comprising said infected olfactory neurons by detecting said marker protein;
   b) isolating said nasal epithelium in vitro;
   c) exposing said infected neurons in said nasal epithelium of the test mammal to either a candidate compound or a standard odorant, and exposing uninfected olfactory sensory neurons in intact control nasal epithelium of a control mammal, which is the same species as the test mammal, in situ to either a candidate compound or a standard odorant;

d) measuring an electrochemical response by said infected neurons in situ in response to said candidate compound, or to said standard odorant and by said uninfected neurons, in situ in response to said candidate compound and to said standard odorant; and e) comparing the measurements of said electrochemical response by said infected neurons, and by said uninfected neurons, each in response to said condidate compound relative to said standard odorant, the measurement of said uninfected neurons in response to said candidate compound relative to said standard odorant indicating whether said candidate compound is a ligand for said odorant receptor.

55. A method for screening for ligands of a G protein-coupled odorant receptor of a mammal comprising:

a) providing a mammal whose olfactory sensory neurons in intact nasal epithelium have been infected with an adenoviral expression vector comprising nucleotide sequences encoding said odorant receptor and a marker protein that can be directly detected by visual inspection, thereby producing infected olfactory neurons which express both said odorant receptor and marker protein and identifying a location on said nasal epithelium comprising said infected olfactory neurons by detecting said marker protein;

b) exposing said infected neurons in said nasal epithelium of the test mammal in situ to either a candidate compound or a standard odorant, and exposing uninfected olfactory sensory neurons in intact control nasal epithelium of a control mammal, which is the same species as the test mammal, in situ to either a candidate compound or a standard odorant;

c) measuring an electrochemical response by said infected neurons in situ in response to said candidate compound, or to said standard odorant and by said uninfected neurons, in situ in response to said candidate compound and to said standard odorant; and d) comparing the measurements of said electrochemical response by said infected neurons, and by said uninfected neurons, each in response to said condidate compound relative to said standard odorant, the measurement of said uninfected neurons in response to said candidate compound relative to said standard odorant indicating whether said candidate compound is a ligand for said odorant receptor.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 27 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

CCCTCGAGTA TGGAGCGAAG GAACCAC                                         27

(2) INFORMATION FOR SEQ ID NO:2:

(i) SEQUENCE CHARACTERISTICS:
        (A) LENGTH: 27 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

GCTCTAGACT AACCAATTTT GCTGCCT                                         27

(2) INFORMATION FOR SEQ ID NO:3:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

-continued

ATTACCGAAG AAATGGCCGC                                               20

(2) INFORMATION FOR SEQ ID NO:4:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CCCATTTAAC ACACGCCATG CA                                            22